United States Patent [19]

Pelosi, Jr.

[11] 4,066,668
[45] Jan. 3, 1978

[54] 5-(4-CHLOROPHENYL)-2-FURIMIDIC ACID HYDRAZIDES

[75] Inventor: Stanford S. Pelosi, Jr., Norwich, N.Y.

[73] Assignee: Morton-Norwich Products, Inc., Norwich, N.Y.

[21] Appl. No.: 779,612

[22] Filed: Mar. 21, 1977

[51] Int. Cl.² ............................................. C07D 307/68
[52] U.S. Cl. .............................. 260/347.3; 260/347.7; 424/285
[58] Field of Search ........................... 260/347.3, 347.7

[56] References Cited

U.S. PATENT DOCUMENTS 3,196,165  7/1965  Burch ................................. 260/347.3

OTHER PUBLICATIONS

McOmie, Protective Groups in Organic Chemistry, Plenum Press, New York, (1973), pp. 46–49.

Primary Examiner—Richard L. Raymond
Attorney, Agent, or Firm—Anthony J. Franze

[57] ABSTRACT

Certain 5-(4-chlorophenyl)-2-furimidic acid hydrazides of the formula:

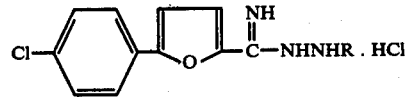

wherein R represents hydrogen or formyl are effective anti-inflammatory agents.

3 Claims, No Drawings

5-(4-CHLOROPHENYL)-2-FURIMIDIC ACID HYDRAZIDES

This invention relates to chemical compounds. More particularly, this invention relates to certain 5-(4-chlorophenyl)-2-furimidic acid hydrazides of the formula:

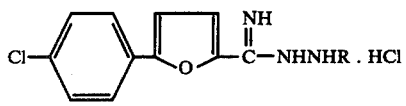

wherein R represents hydrogen or formyl and a method for their preparation. The compounds of this ivention possess pharmacologic activity. They are particularly useful as anti-inflammatory agents as evidenced by their ability to inhibit edema induced in rats by the administration of carrageenin. Thus, when administered at a dose of 300 mg/kg suspended in a vehicle such as aqueous methyl cellulose per os to rats receiving carrageenin, edema associated with that substance is inhibited by 42–55% [Winter et al., P.S.E.B.M. 111:544 (1962)].

The compounds of this invention are readily prepared. Currently, it is preferred to prepare the compounds wherein R is formyl by reacting ethyl 5-(4-chlorophenyl)-2-furimidate hydrochloride with formic acid hydrazide in the presence of triethylamine and a solvent such as ethanol. When R represents hydrogen, it is currently preferred to react 5-(4-chlorophenyl)-N-formamido-2-furamidine with hydrogen chloride in the presence of a solvent such as methanol.

In order that this invention may be fully available to and understood by those skilled in the art, the methods now preferred for making them are described.

EXAMPLE I 5-(4-Chlorophenyl)-N-formamido-2-furamidine

To a mixture of 120 g (0.42 mole) of ethyl 5-(4-chlorophenyl)-2-furimidate hydrochloride in 700 ml of absolute ethanol was added dropwise 62 ml (0.46 mole) of triethylamine at a temperature of 2°–4° while under a nitrogen atmosphere. To this stirring mixture was added portionwise 28 g (0.47 mole) of formic acid hydrazide while maintaining the temperature at 4°–7° by means of an ice bath. The mixture was kept at 5°–7° for 15 minutes, allowed to warm to 23° over a 2½ hour period, cooled to 10°, filtered, and washed in stirring S.D.A #32 to yield 52 g (47%). An analytical sample was prepared by drying a sample in a vacuum pistol with refluxing chloroform, m.p. 155°–157° (Mel-Temp).

Anal. Calcd. for $C_{12}H_{10}ClN_3O_2$: C, 54.66; H, 3.82; N, 15.94. Found: C, 54.92; H, 3.83; N, 15.90.

EXAMPLE II 5-(4-Chlorophenyl)-2-furimidic Acid Hydrazide Hydrochloride

To 500 ml of methanolic HCl was added portionwise 263 g (0.99 mole) of the compound of Example I. The resulting mixture was heated overnight at 55°, cooled, filtered, washed with cold $CH_3OH$, and dried at 60° to yield 26 g (97%). An analytical sample was prepared by recrystallizing a sample from S.D.A. #32/Darco, m.p. 256°–257°.

Anal. Calcd. for $C_{11}H_{10}ClN_3O\cdot HCl$: C, 48.55; H, 4.07; N, 15.44. Found: C, 48.22; H, 4.15; N, 15.23.

What is claimed is:

1. A compound of the formula:

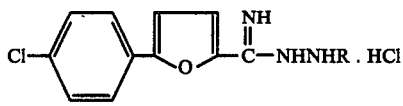

wherein R represents hydrogen or formyl.

2. The compound 5-(4-chlorophenyl)-N-formamido-2-furamidine.

3. The compound 5-(4-chlorophenyl)-2-furimidic acid hydrazide hydrochloride.